United States Patent [19]

Lane et al.

[11] Patent Number: 4,834,758
[45] Date of Patent: May 30, 1989

[54] BONE PROSTHESIS FOR THE LEG AND THIGH

[75] Inventors: Joseph M. Lane, New York, N.Y.; Albert H. Burstein, Stamford, Conn.; James C. Otis, Stamford, Conn.; Timothy M. Wright, Stamford, Conn.

[73] Assignee: New York Society for the Relief of the Ruptured and Crippled, Maintaining the Hospital for Special Surgery, New York, N.Y.

[21] Appl. No.: 199,003

[22] Filed: May 26, 1988

[51] Int. Cl.⁴ .......................... A61F 2/30; A61F 2/38; A61F 2/32

[52] U.S. Cl. ...................................... 623/18; 623/20; 623/23

[58] Field of Search ....................... 623/18, 20, 21, 22, 623/23

[56] References Cited

U.S. PATENT DOCUMENTS

| | | | |
|---|---|---|---|
| 3,696,446 | 10/1972 | Bousquet et al. | 623/20 |
| 3,765,033 | 10/1973 | Goldberg et al. | 623/20 |
| 3,824,630 | 7/1974 | Johnston | 623/20 |
| 3,837,009 | 9/1974 | Walker | 623/20 |
| 3,886,601 | 6/1975 | Findlay | 623/20 |
| 3,996,624 | 12/1976 | Noiles | 623/20 |
| 4,112,522 | 9/1978 | Dadurian et al. | 623/20 |
| 4,301,553 | 11/1981 | Noiles | 623/20 |
| 4,538,305 | 9/1985 | Engelbrecht et al. | 623/20 |
| 4,764,171 | 8/1988 | Harder et al. | 623/20 |

Primary Examiner—Richard J. Apley
Assistant Examiner—David J. Isabella

Attorney, Agent, or Firm—Brumbaugh, Graves, Donohue & Raymond

[57] ABSTRACT

A bone prosthesis for the leg and thigh comprises a distal femoral component that includes a body portion adapted to replace a resected portion of the distal femur and a condylar portion having a spherical surface along its inferior and posterior aspects and an axle hole extending through it in the latero-medial direction at the geometric center of the sperical surface and a proximal tibial component that includes a metal head portion having a cavity opening superiorly and defined by spaced-apart lateral and medial flange portions, each of which has an axle hole. A plastic tibial plateau insert is received in the cavity of the tibial head portion and has a spherical seat matching, receiving and pivotably supporting the femoral condylar spherical surface. A plastic bushing is received in the axle hole of each tibial flange portion, and a metal axle is received in the femoral and tibial axle holes. Clearances between the bushings and the portions of the axle received in the bushings provide latero-medial flexural and axial rotational laxities in the prosthetic joint throughout the range of flexural motion. A shaft component is used interchangeably to replace portions of the tibial and femoral shafts. A diaphysis component is provided or total femoral replacement. A proximal femoral component, used in conjunction with the shaft component or diaphysis component, replaces the femoral part of the hip joint. Identical Morse-type taper couplings are used to connect shaft components to joint components.

13 Claims, 11 Drawing Sheets

BONE PROSTHESIS FOR THE LEG AND THIGH

BACKGROUND OF THE INVENTION

In many cases of severe disease or injury of the bones of the thigh or leg in the region of the knee joint one mode of treatment is to remove the knee joint and part of the adjacent shaft of either the femur or tibia or both and implant a prosthesis. The loss of many of the ligaments and tendons that impart stability to the anatomical knee joint means that the prosthesis must be designed to restrict motions that are normally restricted by those tissues. Various designs of constrained knee joint prostheses have been proposed, some examples being described and shown in the following U.S. Pat. Nos. 3,696,446; 3,765,033; 3,824,630; 3,837,009; and 4,112,522.

It is well-known (see, for example, U.S. Pat. No. 3,837,009) that a simple hinge is a poor choice for a constrained knee joint prosthesis, inasmuch as the anatomical knee joint provides not only for antero-posterior flexure between the femur and tibia but for axial rotation and latero-medial flexure (lateral angulation). It is also recognized that wear of articulating surfaces that are subject to relative movement and large load transfers is minimized by avoiding metal-to-metal contact and making one of the surfaces of plastic. This concept has not ordinarily been extended to control surfaces where loads are minimal and sliding contact sporadic.

Bone and joint replacements for severely diseased or injured thighs or legs where the femoral or tibial shafts are involved, a common case being bone cancer, often call for custom-made prostheses. The costs of designing and fabricating a custom prosthesis are considerable. Moreover, some conditions of the thigh or leg that govern the particular design re not always fully known in advance of surgery, so it is possible that the costly custom prosthesis on hand at surgery may not be optimally suited for the patient.

SUMMARY OF THE INVENTION

One object of the present invention is to minimize all wear in a constrained knee joint prosthesis, not only at the load-transferring surfaces but the control surfaces as well. Another object is to provide a prothesis system of a modular construction in which standard (as distinguished from custom) interchangeable components enable final decisions on the exact configuration of the prosthesis to be made at surgery. Yet another object is to provide for controlled axial rotation and lateral angulation throughout the range of flexure.

The foregoing objects are attained, according to the present invention, by a bone prosthesis for the leg and thigh that comprises at least the following components:

(1) a distal femoral component that includes a body portion adapted to replace a resected portion of the distal femur, and a condylar portion having a spherical surface along its inferior and posterior aspects and an axle hole extending through it in the latero-medial direction at the geometric center of the spherical surface;

(2) a proximal tibial component that includes a metal head portion adapted to replace a resected portion of the proximal tibia and having a cavity opening superiorly and defined in part by spaced-apart lateral and medial flange portions, each of which has an axle hole;

(3) a plastic tibial plateau insert received in the cavity of the tibial head portion and having a spherical seat matching, receiving and pivotably supporting the femoral condylar spherical surface;

(4) a plastic bushing received in the axle hole of each tibial flange portion; and (5) a metal axle received in the femoral and tibial axle holes, there being clearances between the bushings and the portions of the axle received in the bushings to provide latero-medial flexural and axial rotational laxities in the prosthetic joint throughout the range of flexural motion.

In preferred embodiments of the invention the prothesis includes the following features and additional components:

(a) the tibial plateau insert has an anteriorly located, laterally elongated superior stop surface engageable by an inferior/anterior laterally elongated stop surface on the femoral condylar portion at full extension of the prosthetic joint for stability and prevention of hyperextension.

(b) the center lines in the vertical direction of the bushings are located above the geometric center of the spherical surface.

(c) the distal femoral component further includes a stem portion extending superiorly from the body portion and adapted to be received in the medullary cavity of the distal femoral shaft.

(d) the prosthesis further comprises a distal femoral shaft component adapted to replace a resected portion of the distal femoral shaft and having a stem portion at its proximal end adapted to be received in the medullary cavity of the vestigial femoral shaft and means at the distal end of the shaft component and the proximal end of the body portion of the distal femoral component for connecting the distal femoral component to the distal femoral shaft component.

(e) the coupling means referred to in (d) above includes a Morse-type tapered joint and a retaining collar engaging a shoulder on the shaft component, threaded onto the body portion and locked to the body portion against unthreading.

(f) the proximal tibial component further includes a stem portion extending inferiorly from the head portion and adapted to be received in the medullary cavity of the tibial shaft.

(g) the prosthesis further includes a tibial shaft component adapted to replace a resected portion of the proximal tibial shaft and having a stem portion at its distal end adapted to be received in the medullary cavity of the vestigial tibial shaft, and means for connecting the proximal end of the tibial shaft component to the inferior end of the proximal tibial component.

(h) the coupling means referred to in (g) above includes a Morse-type tapered joint and a retaining collar engaging a shoulder on the shaft component, threaded onto the proximal tibial component and locked to the proximal tibial component against unthreading.

(i) the prosthesis further comprises a proximal femoral component adapted to replace a resected proximal portion of the femur and including a body portion and a neck portion, the neck portion having a male Morse-type tapered stem adapted to receive a prosthetic hip joint ball component, a proximal femoral shaft component adapted to replace a resected portion of the proximal femoral shaft, and means for connecting the proximal end of the shaft component to the proximal femoral component.

(j) the coupling means referred to in (i) above includes a Morse-type tapered joint and a retaining collar engaging a shoulder on shaft component, threaded onto the proximal femoral component and locked to the proximal femoral component against unthreading.

(k) the prosthesis further comprises a proximal femoral component adapted to replace the proximal femoral head and including a body portion and a neck portion, the neck portion having a male Morse-type tapered stem adapted to receive a prosthetic hip joint ball component, a femoral shaft component adapted to replace the femoral shaft, means for connecting the proximal end of the femoral shaft component to the proximal femoral component, and means for connecting the distal end of the femoral shaft component to the distal femoral component.

(l) both of the connecting means referred to in (k) above comprise a Morse-type tapered joint and a retaining collar engaging a shoulder on the shaft component, threaded onto the respective distal and proximal femoral components and locked to them against unthreading.

(m) the femoral shaft component is composed of two parts, one of which is of a standard length and the other of which is custom-made to a selected length to provide a desired total length, and the two parts are connected by a pin and socket joint.

For a better understanding of the invention reference may be made to the following description of an exemplary embodiment, taken in conjunction with the accompanying drawings.

DESCRIPTION OF THE DRAWINGS

All of the figures of the drawings are photoreproductions of computer-generated mechanical drawings of the embodiment made by computer-aided design ("CAD"). The dimensions and notes have, of course, been deleted, but deletion of arc centers (shown by crosses), some unused section designation lines, and a few axes designations was impracticable. They can be ignored.

FIGS. 1 to 10 are views of a left distal femoral component with a fixation stem, as follows.

FIGS. 11 to 14 are views of a left distal femoral component with a socket for connection to a femoral shaft component, as follows.

FIGS. 15 to 21 are views of a proximal tibial component with fixation stem, as follows.

FIGS. 22 to 25 are views of a left plastic tibial insert component, as follows.

FIGS. 31 to 34 are views of a tibial component with socket, as follows.

FIGS. 35 to 41 are views of a shaft component, as follows.

FIGS. 42 to 49 are views of the sockets of the Morse-type taper joints used in several components of the prosthesis, as follows:
FIGS. 50 to 53 are views of a retaining collar for the Morse-type taper joints of the prosthesis, as follows.

FIGS. 57 to 65 are views of a left proximal femoral component, as follows.

DESCRIPTION OF THE EMBODIMENT

One important concept of the present invention is to provide a range of stock components that can be used selectively to replace, as required, the anatomical knee joint, a proximal part of the tibial shaft, distal and femoral parts of the femoral shaft, all of the femoral shaft, and the femoral part of the hip joint.

The foregoing concept is advanced in a practical way by using the same connector system for connecting shaft components to joint components, maximizing left-right interchangeability of components and minimizing the differences in those components that must be produced in left and right versions.

Figure 1:
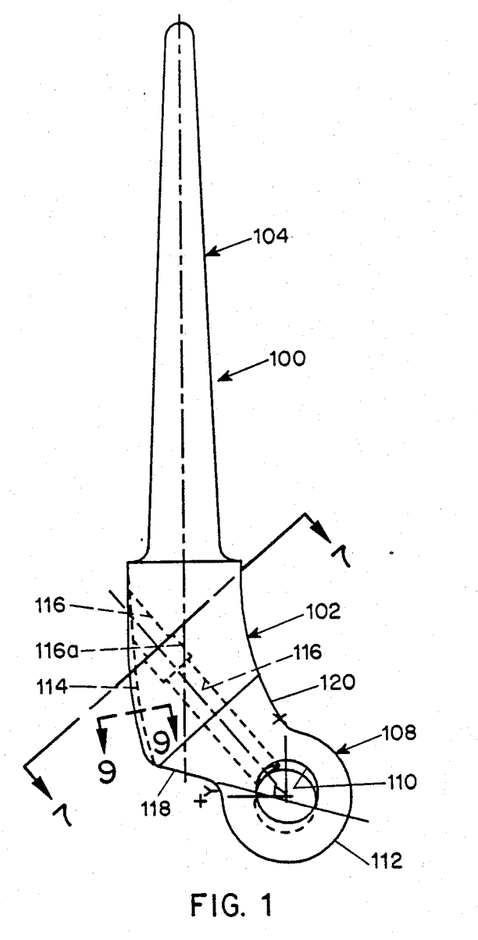
FIG. 1—elevational of the lateral aspect.
Figure 2:
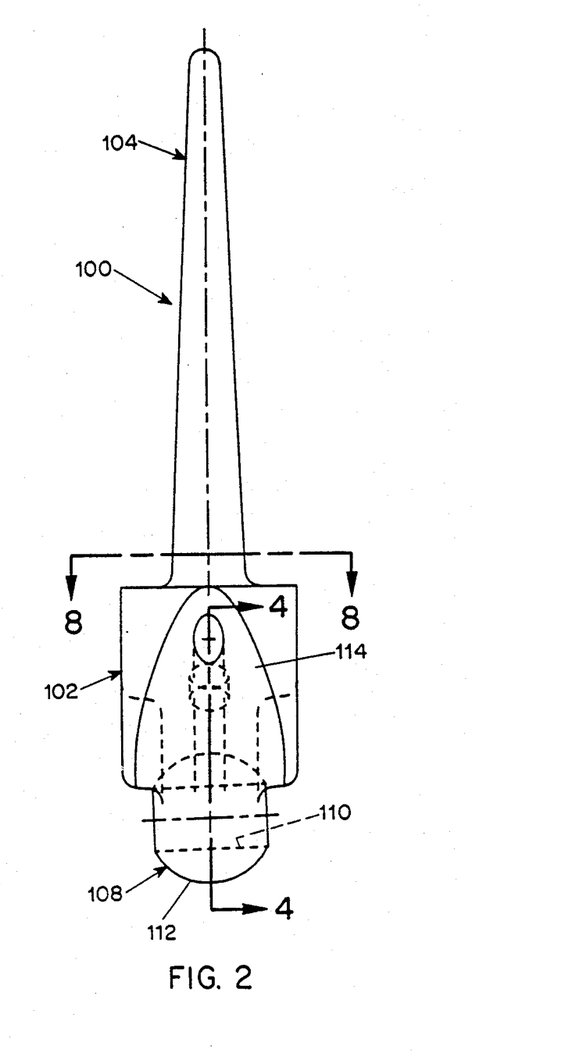
FIG. 2—elevational of the anterior aspect.
Figure 3:
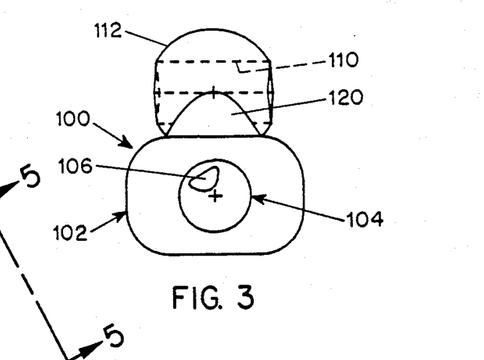
FIG. 3—plan of the superior aspect.
Figure 4:
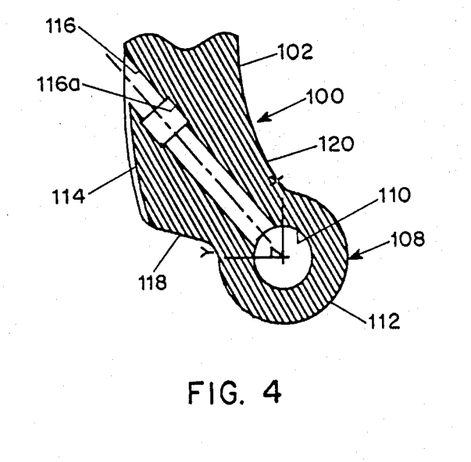
FIG. 4—cross-sectional along 4—4 of FIG. 2.
Figure 5:
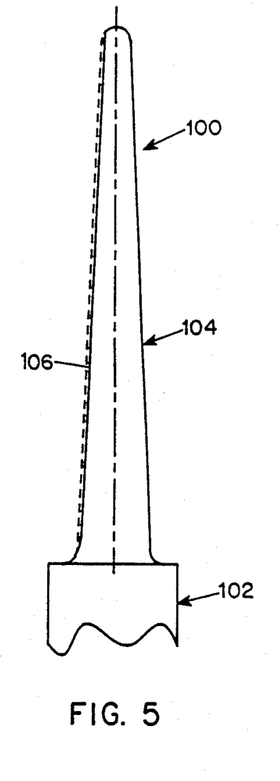
FIG. 5—partial oblique side elevational viewed along 5—5 of FIG. 3.
Figure 6:
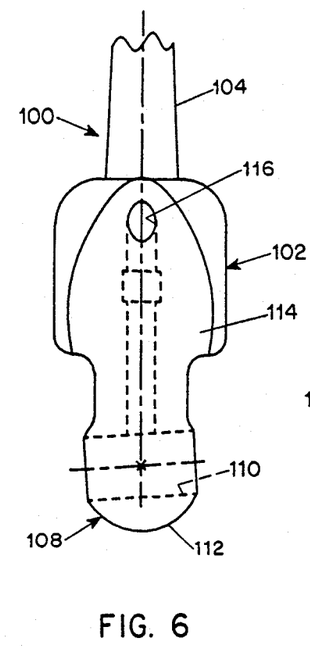
FIG. 6—oblique front elevational viewed orthogonally to the hole for the axle-retaining pin (described below)
Figure 7:
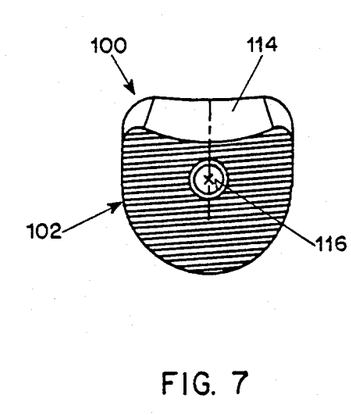
FIG. 7—cross-sectional along 7—7 of FIG. 1.
Figure 8:
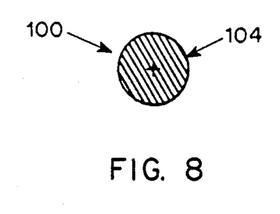
FIG. 8—sectional along 8—8 of FIG. 2.
Figure 9:
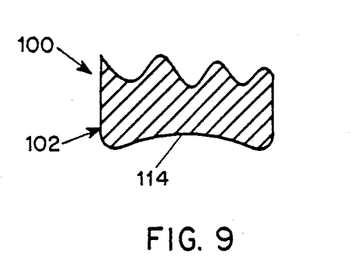
FIG. 9—partial sectional along 9—9 of FIG. 1.
Figure 10:
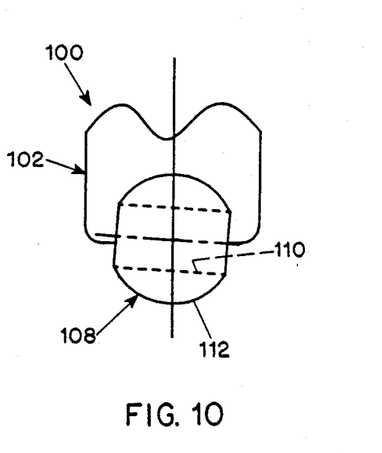
FIG. 10—partial anterior elevational.
Figure 11:
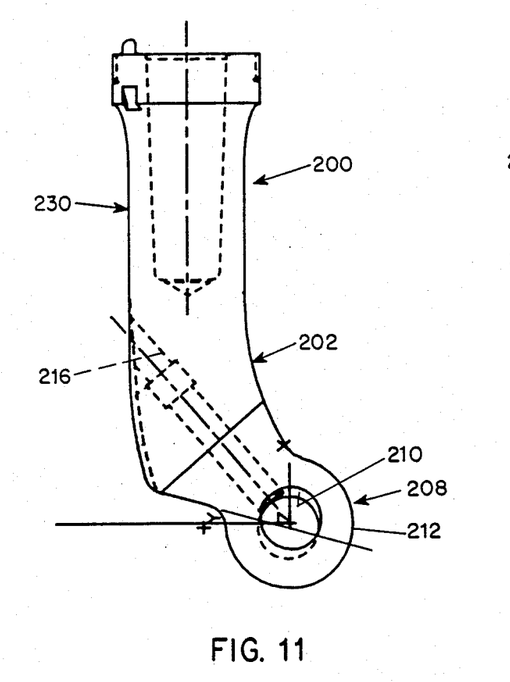
FIG. 11—elevational of the lateral aspect.
Figure 12:
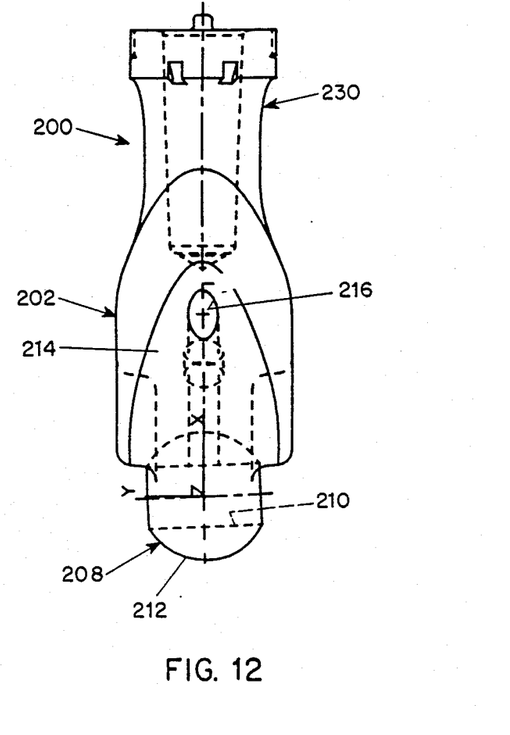
FIG. 12—anterior elevational.
Figure 13:
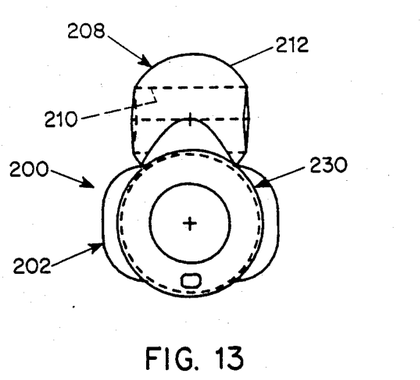
FIG. 13—superior plan.
Figure 14:
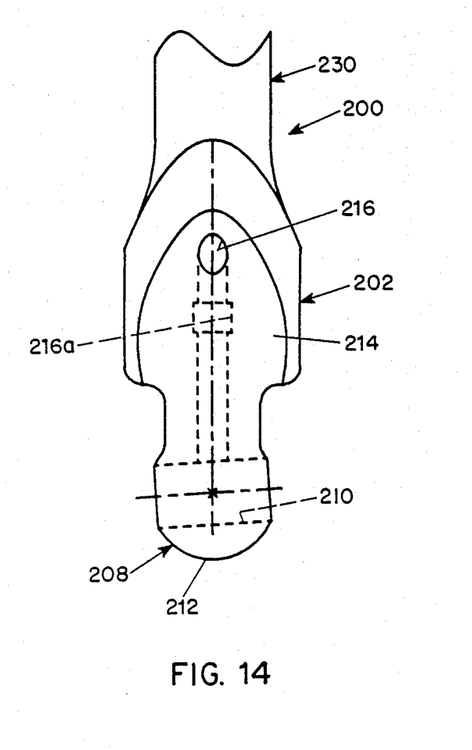
FIG. 14—anterior elevational viewed orthogonally to the centerline of the hole for the axle-retaining pin.
Figure 15:
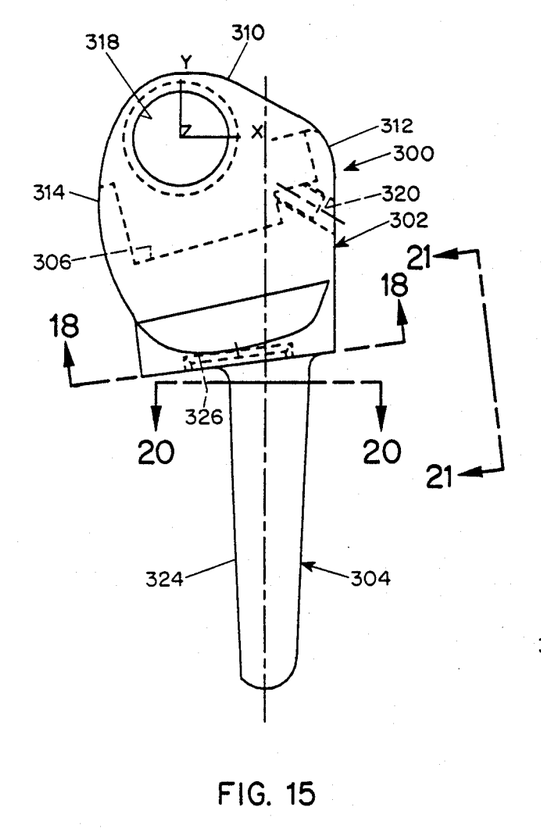
FIG. 15—elevational of the medial aspect when used in left leg (see below)
Figure 16:
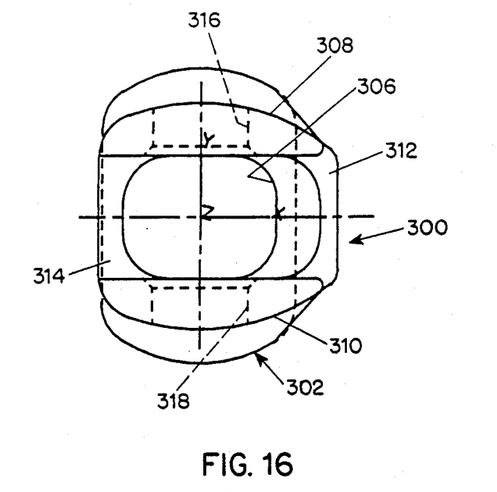
FIG. 16—plan of the superior aspect.
Figure 17:
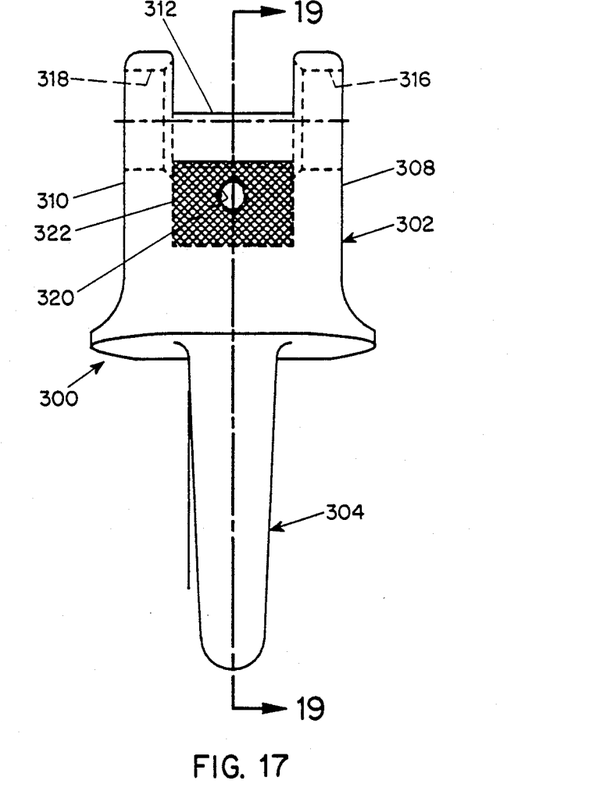
FIG. 17—elevational of the anterior aspect.
Figure 18:
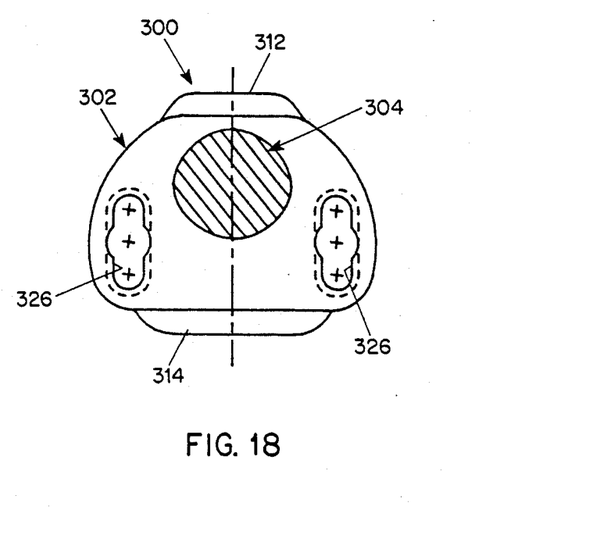
FIG. 18—cross-sectional along 18—18 of FIG. 15.
Figures 19, 20:
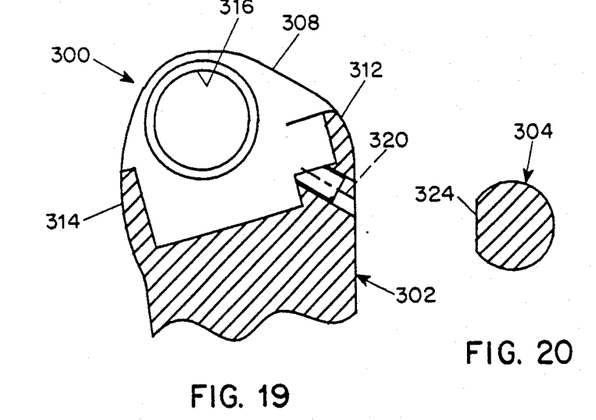
FIG. 19—partial cross-sectional along 19—19 of FIG. 17.
FIG. 20—cross-sectional along 20—20 of FIG. 15.
Figure 21:
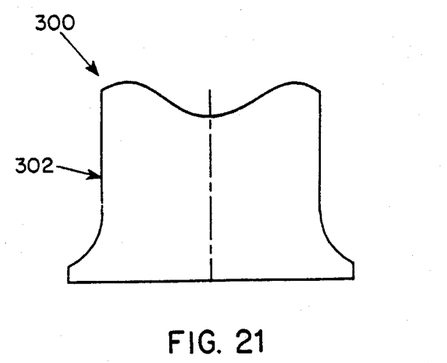
FIG. 21—partial oblique front elevational along 21—21 of FIG. 15.
Figure 22:
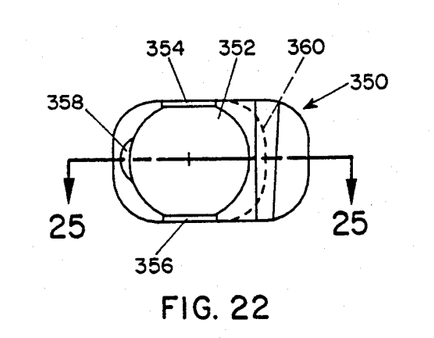
FIG. 22—superior plan.
Figure 23:
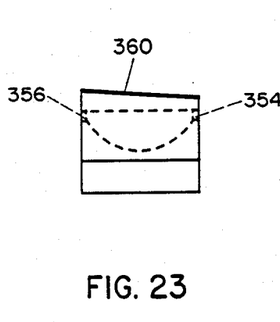
FIG. 23—anterior elevational.
Figure 24:
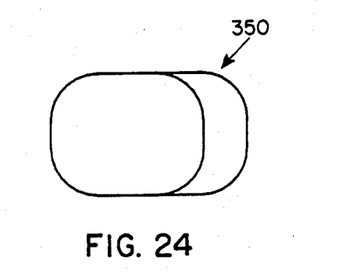
FIG. 24—inferior plan.
Figure 25:
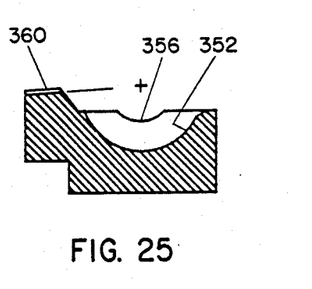
FIG. 25—cross-sectional along 25—25 of FIG. 22.
Figure 26:
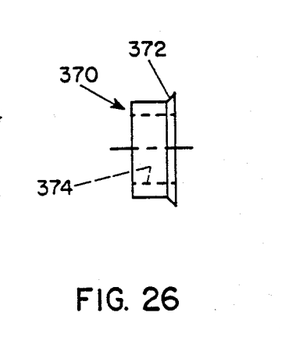
FIGS. 26 and 27 are side and end elevational views, respectively, of a plastic bushing for the tibial component.
Figure 27:
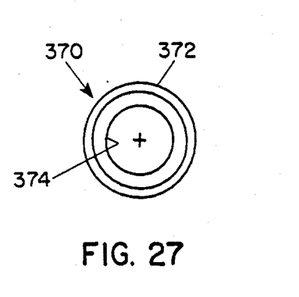
Figure 28:
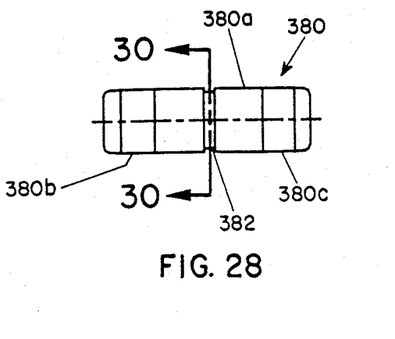
FIGS. 28 and 29 are side and end elevational views, respectively, of an axle.
Figure 29:
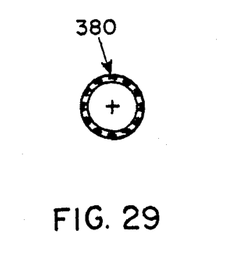
Figure 30:
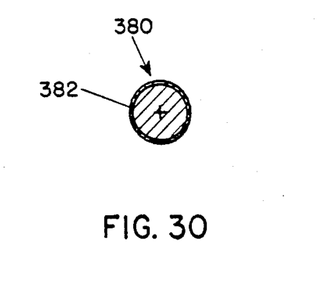
FIG. 30 is a cross-sectional of the axle along lines 30—30 of FIG. 28.
Figure 31:
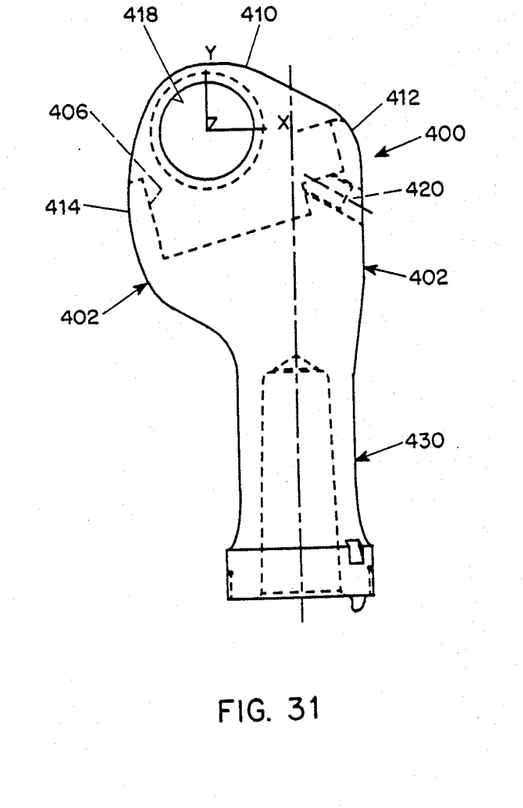
FIG. 31—elevational of the medial aspect (when used in left leg)
Figure 32:
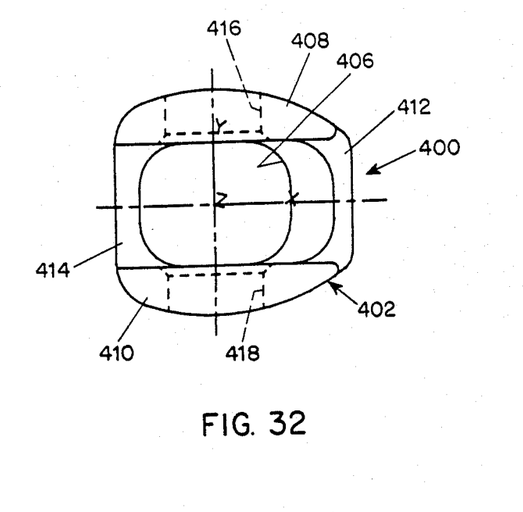
FIG. 32—superior plan.
Figure 33:
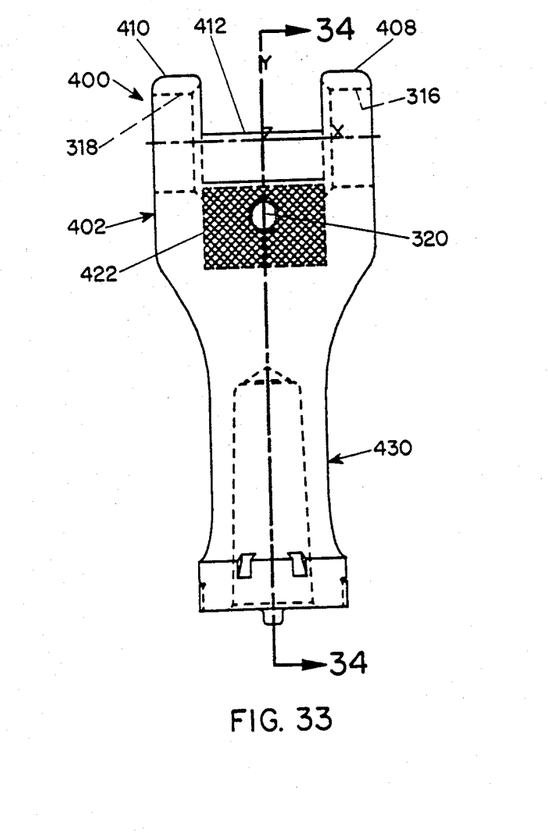
FIG. 33—anterior elevational.
Figure 34:
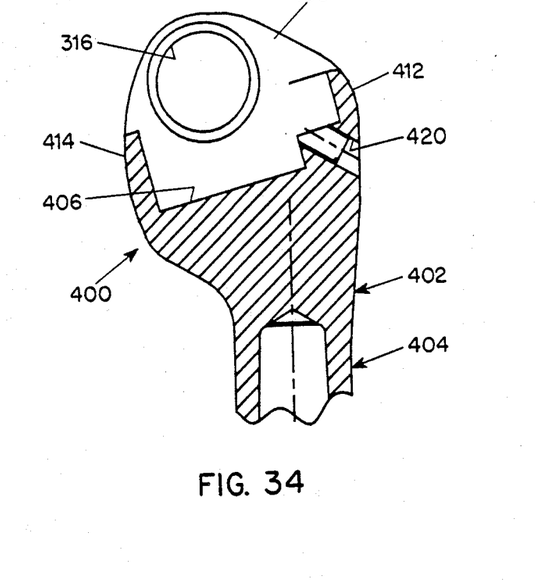
FIG. 34—partial cross-sectional along 34—34 of FIG. 33.
Figure 35:
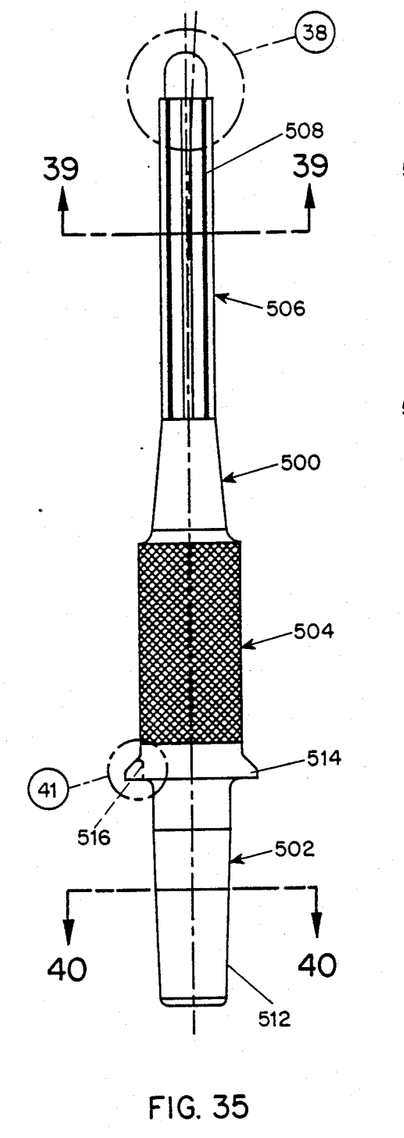
FIG. 35—elevational.
Figure 36:
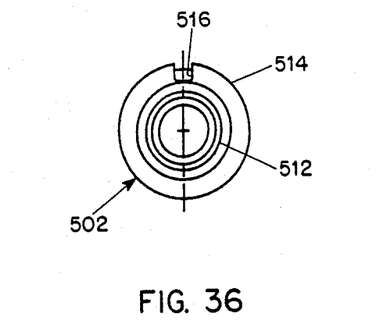
FIG. 36—plan of the connector end.
Figure 37:
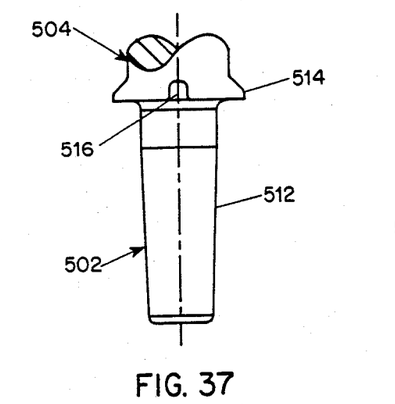
FIG. 37—partial elevational viewed orthogonally to FIG. 35.
Figure 38:
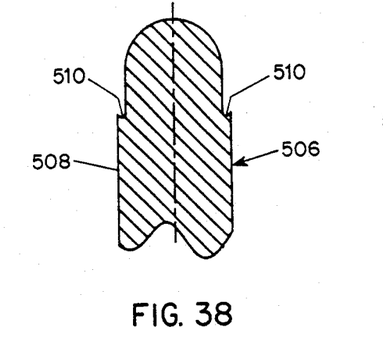
FIG. 38—cross-sectional detail 38 of FIG. 35.
Figure 39:
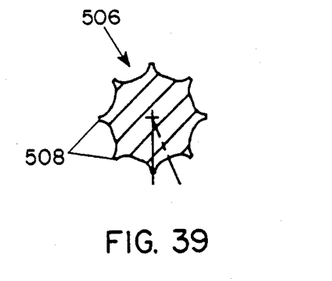
FIG. 39—cross-sectional along 39—39 of FIG. 35.
Figure 40:
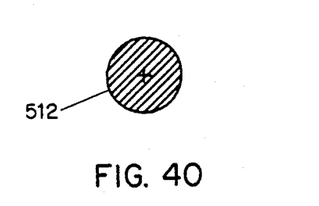
FIG. 40—cross-sectional along 40—40 of FIG. 35.
Figure 41:
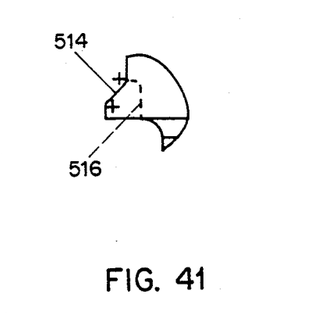
FIG. 41—detail 41 of FIG. 35.
Figures 42, 43, 45, 46, 47:
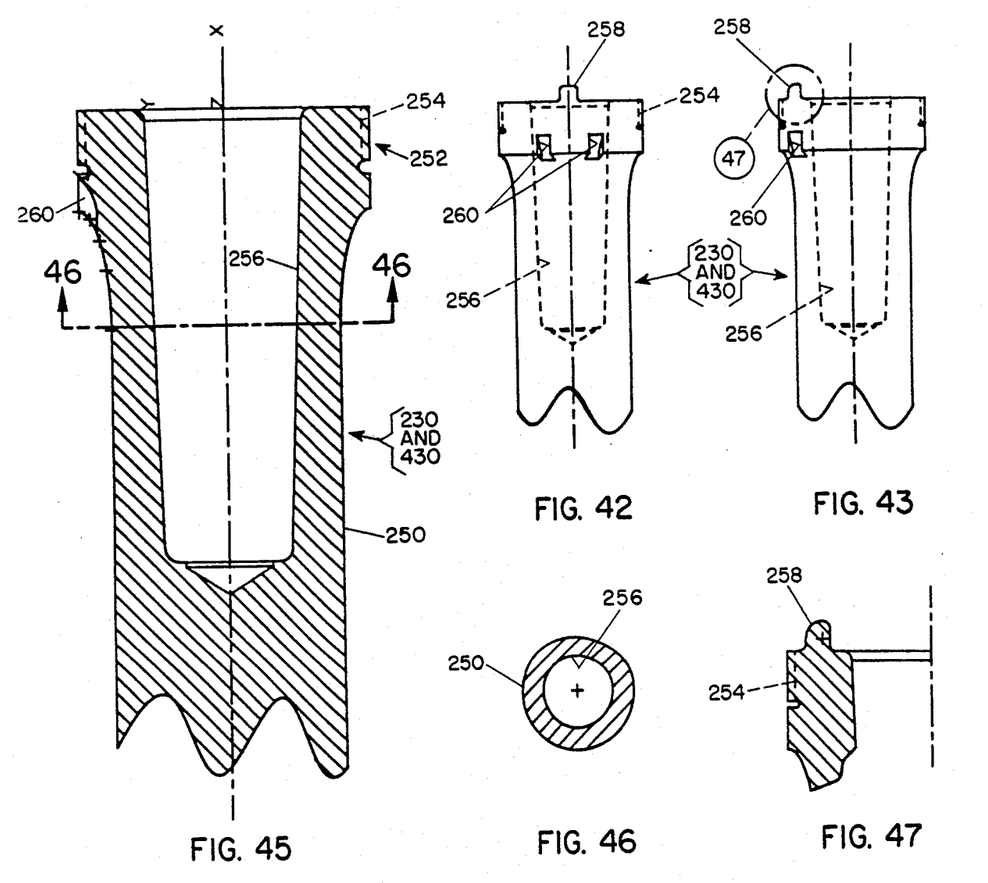
FIGS. 42 and 43—mutually orthogonal elevational views.
FIG. 45—axial cross-sectional along 45—45 of FIG. 44.
FIG. 46—cross-sectional along 46—46 of FIG. 45.
FIG. 47—cross-sectional detail 47 of FIG. 43.
Figure 44:
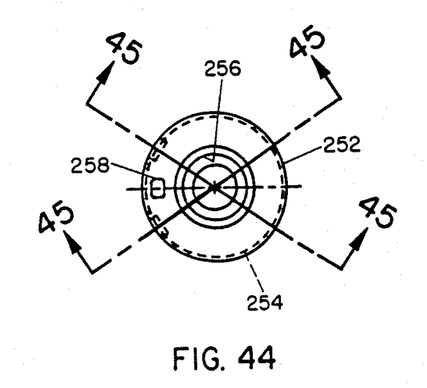
FIG. 44—end elevational.
Figure 48:
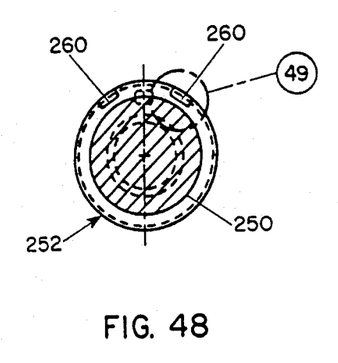
FIG. 48—transverse cross-sectional looking toward the socket opening (from below with respect to FIG. 45)
Figure 49:
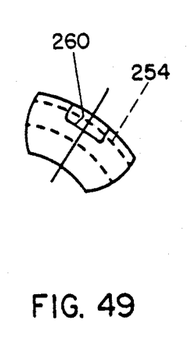
FIG. 49—detail 49 of FIG. 48.
Figure 50:
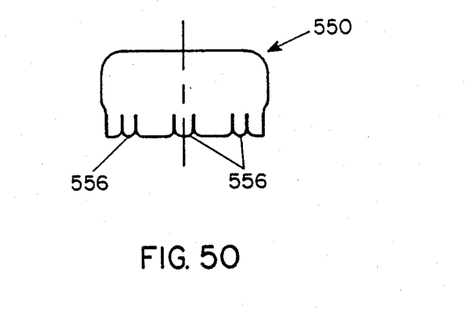
FIG. 50—side elevational.
Figure 51:
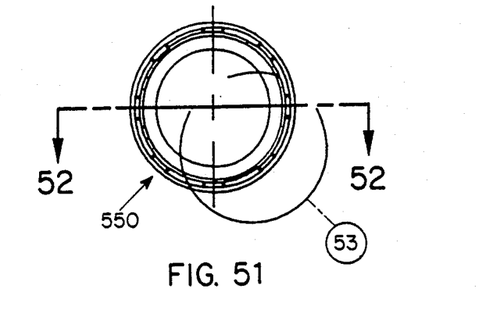
FIG. 51—end elevational.
Figure 52:
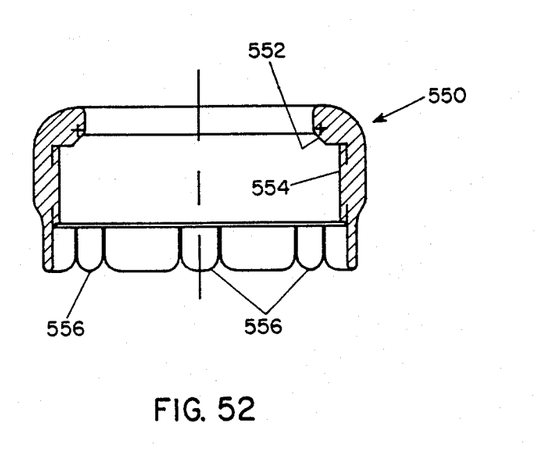
FIG. 52—transverse cross-sectional along 52—52 of FIG. 51 on a larger scale.
Figure 53:
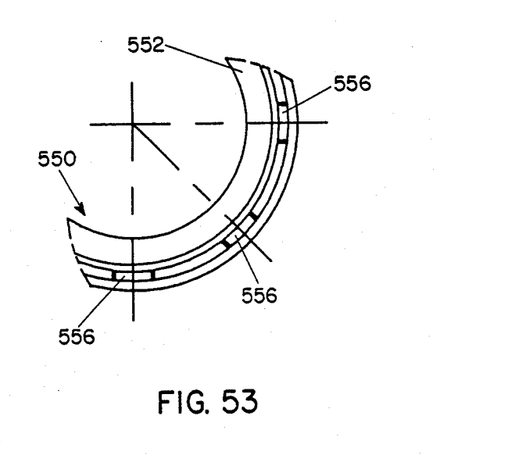
FIG. 53—detail 53 of FIG. 51.
Figure 66:
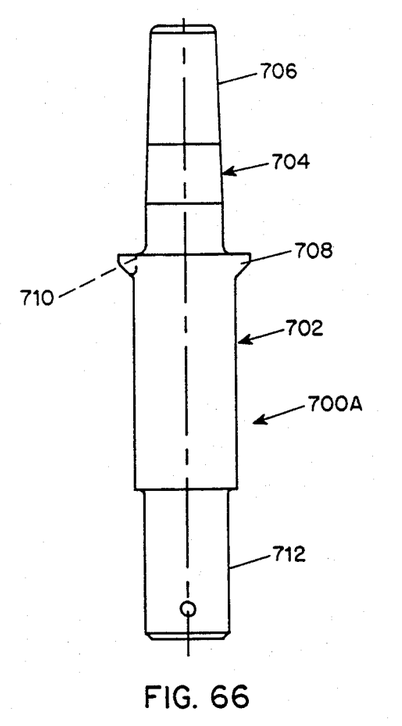
FIGS. 66 and 67 are elevational views of a two-part femoral shaft component.
Figure 67:
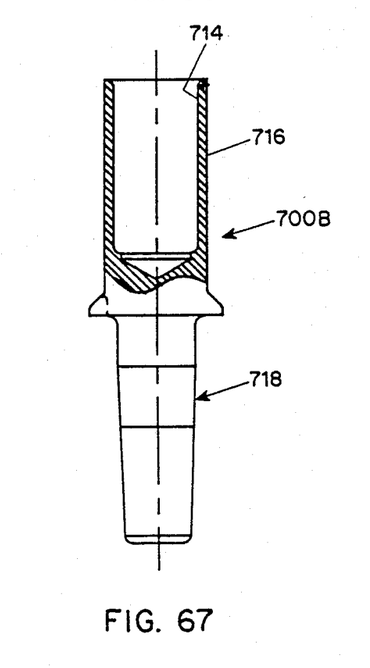

The present invention comprises the following main components:

(1) A distal femoral component with fixation stem (FIGS. 1 to 10), which is used to replace the femoral part of the knee-joint in cases where the treatment does not involve excision and prosthetic replacement of the distal femoral shaft;

(2) A distal femoral component with connector socket (FIGS. 11 to 14), which is used with a shaft component (see below) that replaces the distal part or all of the femur;

(3) A proximal tibial component with fixation stem (FIGS. 15 to 21) that is used to replace the tibial part of the knee joint when the tibial shaft is not involved;

(4) A proximal tibial component with connector socket (FIGS. 31 to 34) for use with a shaft component that replaces part of the proximal tibial shaft;

(5) All configurations of the prosthesis system include a plastic tibial insert component (FIGS. 22 to 25), plastic axle bushings (FIGS. 26 and 27) and a metal axle (FIGS. 28 to 30) for restraint of motions;

(6) A shaft component with fixation stem and connector pin (FIGS. 35 to 41), used interchangeably for the proximal tibial shaft, the distal femoral shaft, and the proximal femoral shaft;

(7) A retaining collar (FIGS. 50 to 53) used for all pin-socket joints in conjunction with special configurations of the pin or socket elements;

(8) A two-part total femoral shaft replacement component (FIGS. 66-67); and (9) A proximal femoral component, which replaces the femoral part of the hip joint.

The distal femoral component with fixation stem 100 comprises a body portion 102 that is approximately rectangular in all major aspects, a fixation stem portion 104 of round cross-section, except for a flat 106 for rotationally stable fixation, and a condylar portion 108 that extends posteriorly and inferiorly from the body portion. An axle hole 110 extends latero-medially through the condylar portion. The axle hole slopes inferiorly in the latero-medial direction, relative to the longitudinal axis of the stem 104, in order to establish the normal valgus angle of the femur relative to the tibia in the assembled prosthesis (see FIGS. 2 and 6). A segment of a spherical surface 112 having its center at the geometric center of the axle hole is presented along the distal and posterior aspects of the condylar portion 108. A concavity 114 along the anterior aspect of the body part 102 provides a nesting area for the tendon of the quadriceps extensor. A hole 116 extending through the body portion from the anterior and into the femoral portion, where it opens to the axle hole, receives an axle-retaining pin, as described below. The inferior surface of the body portion lying anteriorly of the femoral portion is a stop surface 118 at extension of the leg, and a rounded posterior surface of the body (see FIG. 3) at the juncture with the femoral portion provides a stop surface 120 at flexion of the leg. Except for the orientations of the femoral portion 108 and axle hole 110 and the flat 106 on the stem portion, the right and left versions are the same.

The distal femur is excised along a planar cut slightly below the borders of the inner and outer tuberosities, thereby leaving dense bone on the vestigial femoral extremity to transfer loads to the superior surface of the body 102. The component 100 is cemented in place with polymethyl methacrylate cement.

The distal femoral component with connector socket 200 (FIGS. 11 to 14) is the same as the component 100 except that it has a connector socket portion 230 instead of a fixation stem. The parts of the component 200 that are the same as those of the component 100 are designated by numbers in the 200 series but with the same digit and decimal numbers used above, and some of the figures showing the component 100 are applicable to the component 200, as will be apparent to the skilled observers of the drawings. The details of the connector socket 230 are shown in FIGS. 42 to 49 and described below. Suffice it to say at this point that the socket portion 230 provides a means for connecting the component 200 to a shaft component that replaces part or all of the femur.

The tibial component with stem 300 (FIGS. 16 to 21) comprises a head portion 302 that replaces the head portion of the anatomical tibia and a stem portion 304 that is received in the medullary cavity of the proximal tibial shaft. The superior surface of the head portion has a cavity 306 that is defined by lateral and medial flanges 308 and 310 and anterior and posterior flanges 312 and 314. Internally chamfered, axially aligned axle holes 316 and 318 transect the flanges 308 and 310. A threaded hole 320 opens at the anterior aspect for reception of a screw (not shown) by which the patella may be fastened to the component. It is often desirable to fasten the patella to the prosthetic knee joint to improve the performance of the quadriceps muscles in extending the leg. The cross-hatching indicates a coating 322 of porous material (known per se) on the anterior aspect for promoting ingrowth of tissue for enhanced fixation of the patella.

The component 300 is implanted on the tibial plateau by excising the tibial head slightly below the tuberosities along a slightly oblique plane corresponding to the sloping, flat inferior aspect of the head portion 302. Affixation in cement is enhanced by a flat 324 along the stem 304 and cement pockets 326 on the inferior aspect of the head portion.

A tibial insert component 350 (FIGS. 22 to 25) is received in nested relation with a close fit in the cavity 306 of the tibial component 300. A spherical recess 352 having the same radius as the spherical surface 112 of the condylar portion 108 (208) of the femoral component 100 (200) accepts the condylar portion in articular and load-bearing relations. Shallow notches 354 and 356 of the lateral or medial borders of the recess allow the axle (described below) to enter the bushings (also described below). A shallow notch 358 at the posterior margin of the insert serves as a stop surface for restraining hyper-flexion upon engagement by the surface 120 (220) of the femoral component. A slightly sloping stop surface 360 restrains hyper-extension by engaging the stop surface 118 of the femoral component. The slope of the surface 360 conforms to the normal valgus angulation of the femur relative to the tibia. Because of this slope, the tibial insert component 350 must be produced in right and left versions. The tibial component 300 can be used in both legs.

Figure 54:
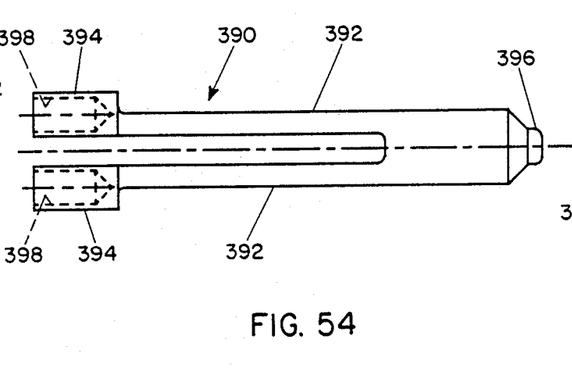
FIGS. 54 to 56 are side and end elevational views of an axle-retainer pin.
Figure 55:
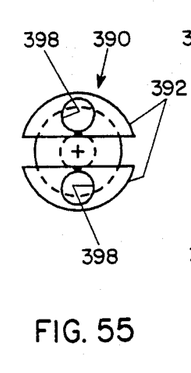
Figure 56:
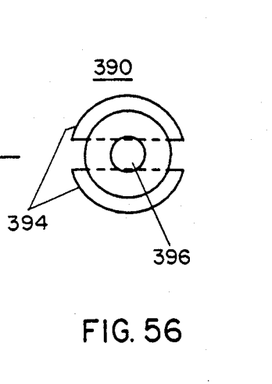
Figure 57:
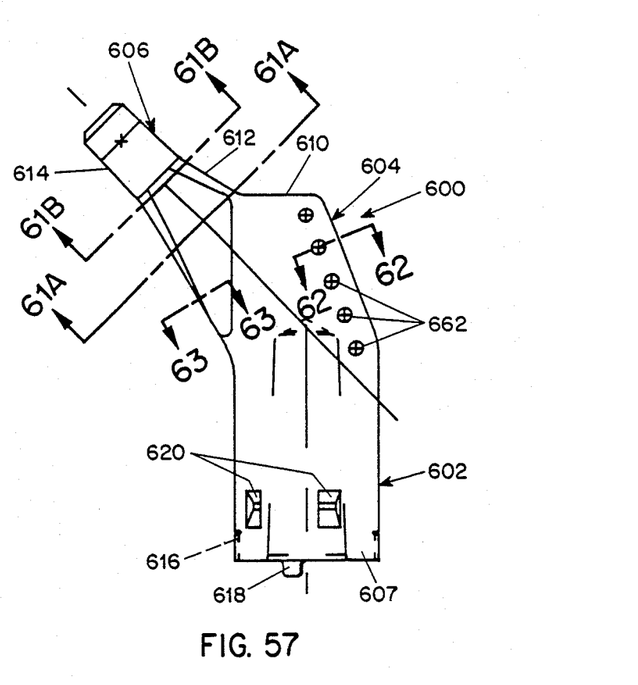
FIG. 57—anterior elevational.
Figure 58:
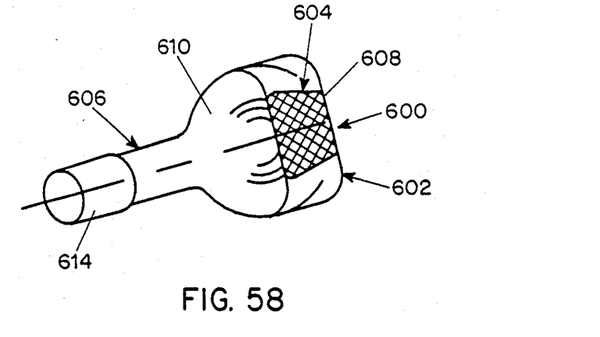
FIG. 58—superior plan.
Figure 59:
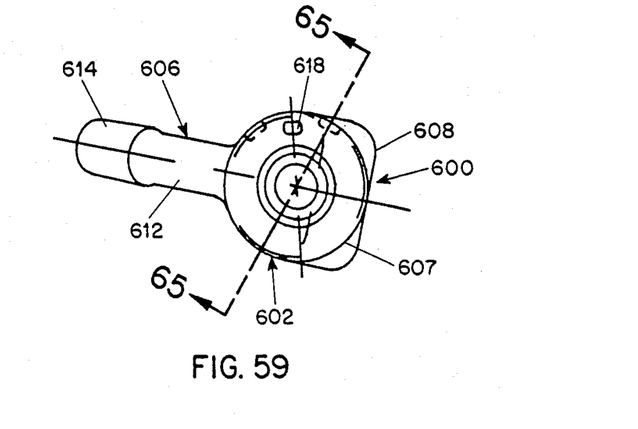
FIG. 59—inferior plan.
Figure 60:
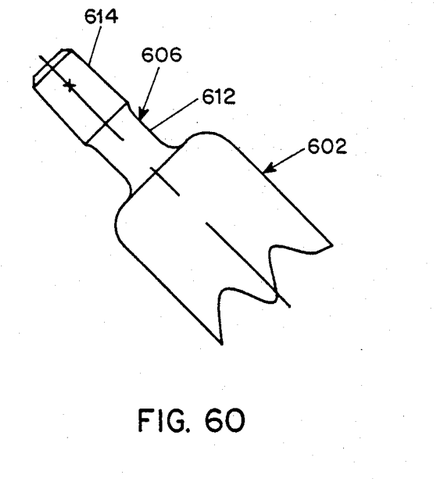
FIG. 60—oblique elevational view of the medial aspect looking orthogonally to the axis of the neck portion.
Figures 61A, 61B:
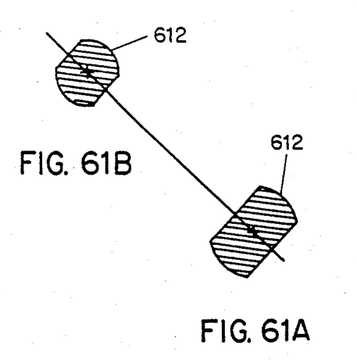
FIGS. 61A and 61B—sectionals indicated in FIG. 57.
Figure 62:
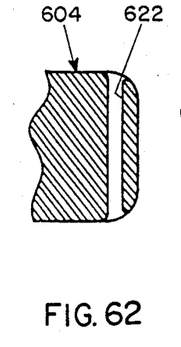
FIGS. 62 and 63—partial sectionals indicated in FIG. 57.
Figure 63:
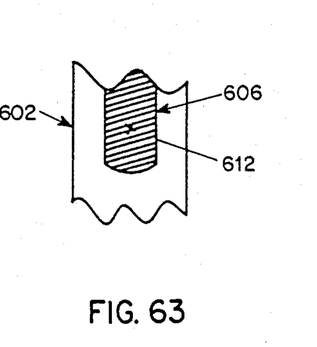
Figure 64:
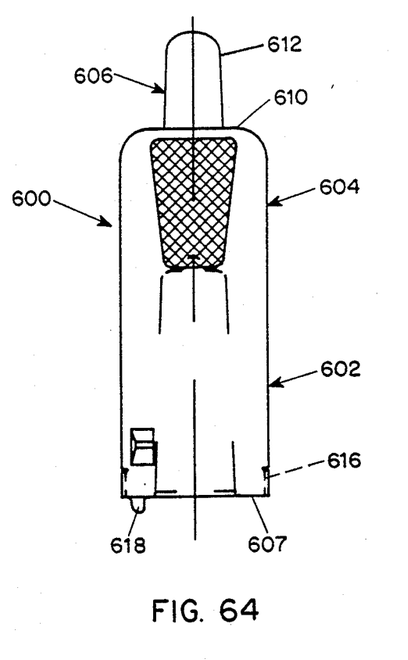
FIG. 64—elevational of the lateral aspect.
Figure 65:
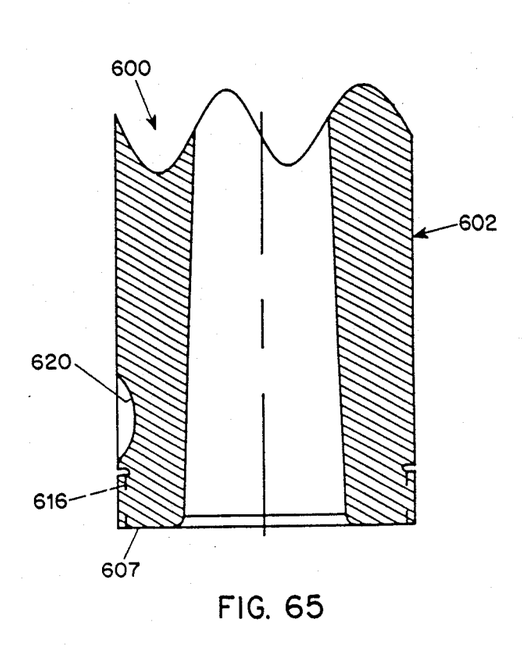
FIG. 65—partial section along 65—65 of FIG. 59.

The axle holes 316 and 318 receive bushings 370 with the edge flanges 372 inward for retention. The bushings 370 are installed before the insert 350, and the insert holds the bushings temporarily in place because of an overlap along the lower portions of the bushings. At final assembly of the prosthesis after implantation of the femoral and tibial elements, an *axle* 380 (FIGS. 28 to 30) is passed through the axle hole 110 (210) in the femoral component and the axle holes 374 in the bushings. An axle-retaining pin 390 (FIGS. 54 to 56) is installed in the hole 116 (216) in the femoral component. The shank of the pin 390 is split into resilient legs 392 that are pressed together to enable the enlarged head 394 to enter the hole 116 (216) and then resile into captured position in the enlarged section 116a of the hole. A tip 396 on the pin 390 engages a groove 382 in the axle 380 and holds the axle in place. The pin 390 is installed with the aid of a pliars-like instrument (not shown) having pins that enter holes 398 in the pin head.

In the assembled prosthesis the components that replace the knee joint provide articulation through a range of motion limited by engagement of the stop surface 118 (218) of the femoral component with the surface 360 of the tibial insert 350 at extension and engagement of the femoral surface 120 with the tibial insert surface 358 at full flexion. The width of the femoral condylar portion 108 (208) is slightly less than the spacing between the internal walls of the tibial flange portions 308 and 310, leaving a lateral clearance that permits lateral angulation and axial rotation throughout the range of motion. At full extension with weight applied, however, the prosthetic joint is highly stable against angulation due to seating of the femoral stop surface 118 (218) on the wide tibial insert surface 360.

Restraints on lateral angulation and axial rotation are provided by engagements between the axle 380, which is received with its medial portion 380a in a close fit with the femoral axle hole 110 (210), and the holes 374 in the respective busings 370, which are in clearance with the tapered end portions 380b and 380c (FIG. 28) of the axle. The center lines of the bushings 370 are above the geometric center of the spherical surface 112 (212) of the femoral condylar surface in the prosthetic joint. Accordingly, upon lateral angulation in both the lateral and medial directions, the axle 380 can bottom-out in one bushing without the other end of the axle topping-out in the other bushing until after the spherical surface of the femoral condylar component is separated from the tibial insert. A lateral moment causing a topping-out of either end of the axle in the corresponding bushing is resisted by the downward force of the patient's weight tending to keep the femoral component seated in the tibial insert. The downward force smooths the rocking motion and absorbs the energy of large lateral movements applied to the prosthetic joint. A lateral angulation and an axial rotation of the order of 10 degrees total in each case are appropriate.

All engagements, both load-bearing and restraining, between relatively moving components of the knee joint are between metal and plastic. All components of the prosthesis system except the tibial insert 350 and the bushings 370 are made of a surgical grade metal, Ti-6Al-4V being preferred. The tibial insert and the bushings are made of ultra high molecular weight polyethylene (UHMW/PE). The metal-plastic surfaces produce low frictional forces for freedom of movement and minimum wear. Engagements at the limits of motions between metal and plastic occur with energy absorption resulting from deformation of the plastic.

When the proximal tibial shaft is to be excised, the proximal tibial component with socket 400 (FIGS. 31 to 34) is used instead of the tibial component with stem 300 described above (FIGS. 15 to 21). The superior portion of the component 400 is the same as the superior portion of the component 300, and reference numerals with the same decimal and digit numbers in the 400 series are assigned. Instead of a stem (304) the component 400 has a socket portion 430 that is configured to accept the pin of a shaft component, as described below. Instead of a broad surface presented inferiorly to bear on the vestigial tibial head, the juncture of the head portion 402 with the shaft portion 404 is smoothly rounded along all aspects. The cement pockets (326) are, of course, omitted.

The shaft component 500 (FIGS. 35 to 41) is used to replace a proximal part of the tibial shaft, a distal part of the femoral shaft or a proximal part of the femoral shaft. It includes a coupling portion 502, a shaft body portion 504 and a fixation stem portion 506. The body portion 504 is an elongated circular cylinder, replaces a resected portion of the bone shaft, and is treated to provide a porous surface, indicated by the cross-hatching, for promotion of tissue ingrowth and adhesion. The stem is formed with longitudinal flutes 508, the tips 510 of which are undercut to form sharp points for cutting their way longitudinally along the medullary canal of the tibial or femoral shaft as the component is implanted by driving the stem into the vestigial bone shaft. The coupling portion consists of a tapered pin 512 that forms the male element of a Morse-type tapered connector and a flange 514 at the juncture with the body portion 504. A notch 516 in the flange receives a lug (described below) on the socket element of the connector and hence is a key-way providing for rotational locking of the connection. The shaft component is made in a range of lengths (e.g. 25 mm increments from 150 mm to 250 mm) by varying the length of the body portion 504.

The socket portions 230 and 430 of the tibial and femoral components 200 and 400, respectively, are identical such that each receives the coupling portion 502 of the shaft component 500. As shown in detail in FIGS. 42 to 49, the socket portions 230 and 430 have a circular cylindrical shank 250 and an enlarged head 252 having external threads 254. A tapered bore 256, the female component of the Morse-type tapered coupling, matches and receives the pin 512 of the component 500. A lug 258 projects from the neck and serves as a key by reception in the notch 516 of the component 500 for maintaining rotational integrity in the coupling.

To insure that the shaft component 500 does not loosen or separate axially from the respective tibial or femoral component to which it is coupled, a collar 550 (FIGS. 50 to 53) is received over the flange 514 of the shaft component, is threaded onto the threads 254 on the head 252 of the socket portion 230 (or 430), and is locked against rotation to the head 252. A shoulder 552 bears against the flange 514, internal threads 554 are received by the threads 254, and one of a series of equally spaced-apart bendable fingers 556 formed by slits in the rim of the collar is bent into one of two circumferentially spaced-apart grooves 260 in the head portion 252 (see FIG. 42) to ensure that the collar does not unthread from the head 252 by working of the muscles or other tissues of the thigh. The circumferential pitch of the fingers is slightly different from that of the two grooves, so the collar can be locked in place within a few degrees rotationally ahead of fully tightened.

It is intended that the shaft component be secured to the proximal tibial or distal femoral component by driving the Morse-type taper coupling home in the operating room after the surgeon makes a final decision on the length of the shaft component to be implanted, based on the observed condition of the bone shaft and the resulting decision of how much of it is to be removed.

Where the patient has a lesion of the femur that calls for a total femoral replacement, the total femoral diaphysis component 700A-700B (FIGS. 66 and 67) and the proximal femoral component 600 (FIGS. 57 to 65) are used with the distal femoral component with socket 400 and the appropriate proximal tibial component. The diaphysis component 700A-700B is assembled by joining a proximal part 700A and a distal part 700B.

The proximal part has an elongated circular cylindrical body 702, a coupling portion 704 at its proximal end, consisting of a tapered pin 706 and a flange 708 with a key-way slot 710, and a straight circular cylindrical coupling pin 712 at its distal end. The length of the body 702 is chosen to fit the diagnostic measurement of the patients's femur. The pin 712 is received with an interference fit in a socket 713 in a circular cylindrical body 716 of the distal part 700B having the same diameter as that of the body 702. A coupling portion 718 on the distal end of the distal part 700B is received in and secured to the socket portion 430 of the distal femoral component. The coupling portion 718 is exactly the same as the coupling portion 502 of the shaft component 500, the description of which given above applies and is not repeated. The parts are assembled in the shop and secured by a passing drive pin (not shown) through the coupling 712-714 and welding the pin in place.

The upper portion of the femur is replaced by the proximal femoral component 600 (FIGS. 57 to 65) having a body portion 602, a trochanteric portion 604 and a neck portion 606. The body 602 is circular at its lower extremity 607 and widens and flattens along its lateral aspects superiorly to an upper juncture 608 with the trochanteric aspect 604. The superior aspect 610 is generally flat, but with rounded margins. The base 612 of the neck portion 606 is of uniform thickness, has flat sides and rounded upper and lower aspects, and tapers in height medially. At the end of the neck base 612 is a tapered pin 614 that receives a prosthetic femoral head (not shown and known per se) by means of a socket forming with the pin 614 a Morse-type tapered joint.

The body 602 serves mainly as a socket for a Morse-type connection (essentially identical to that described above) to the proximal coupling portion 704 of the diaphysis component 700A-700B. The body has external threads 616 for the collar 550, a lug 618 for rotational keying and two notches 620, the appropriate one of which receives a finger 556 of the collar 550 (as described above).

The trochanteric portion 604 has a series of holes 622 through it that receive sutures for fastening the tendons normally inserted into the anatomical great trochanter to the prosthetic component. The cross-hatched area on the trochanteric aspect represents a porous coating (known per se) that promotes tissue ingrowth and adhesion.

The proximal femoral component 600 can be used with the shaft component 500 in treating a lesion of the proximal femoral shaft that does not require excision of the distal femoral shaft.

The location of the lug 618 is established such that it orients the neck of the component 600 obliquely to the latero-medial and the axial axes of the femur—that is, the neck extends medially and anteriorly from the plane of the latero-medial and axial axes (which is anatomically correct). Accordingly one of the components of a partial or total femoral prosthesis for the proximal extremity must be made in left and right versions. It is expedient to make the component 60 in right and left versions, because all that is required is to relocate the keying lug 618 in mirror-image positions. In this case the shaft component 500 can b standardized for all uses in the thigh and leg.

We claim:

1. A bone prosthesis for the leg and thigh comprising a metal distal femoral component that includes a body portion adapted to replace a resected portion of the distal femur and a condylar portion having a spherical surface along its inferior and posterior aspects and an axle hole extending through it in the latero-medial direction at the geometric center of the spherical surface; a metal proximal tibial component that includes a head portion adapted to replace a resected portion of the proximal tibia and having a cavity opening superiorly and defined in part by spaced-apart lateral and medial flange portions, each of which has an axle hole; a plastic tibial plateau insert received in the cavity of the tibial head portion and having a spherical seat substantially matching, receiving and pivotably supporting the femoral condylar spherical surface; a plastic bushing received in the axle hole of each tibial flange portion; and a metal axle received in the femoral and tibial axle holes, there being clearances between the bushings and the portions of the axle received in the bushings to provide latero-medial flexural and axial rotational laxities in the prosthetic joint throughout the range of flexural motion.

2. A prosthesis according to claim 1 wherein the tibial plateau insert has an anteriorly located laterally elongated superior stop surface engageable by an inferior-/anterior laterally elongated stop surface on the femoral condylar portion at full extension of the prosthetic joint for stability and prevention of hyper-extension.

3. A prosthesis according to claim 1 wherein the center lines in the vertical direction of the bushings are located above the geometric center of the spherical surface.

4. A prosthesis according to claim 1 wherein the distal femoral component further includes a stem portion extending superiorly from the body portion and adapted to be received in the medullary cavity of the distal femoral shaft.

5. A prosthesis according to claim 1 and further comprising a distal femoral shaft component adapted to replace a resected portion of the distal femoral shaft and having a stem portion at its proximal end adapted to be received in the medullary cavity of the vestigial femoral shaft and means at the distal end of the shaft component and the proximal end of the body portion of the distal femoral component for connecting the distal femoral component to the distal femoral shaft component.

6. A prosthesis according to claim 4 wherein the coupling means includes a tapered joint and a retaining collar engaging a shoulder on the shaft component, threaded onto the body portion and locked to the body portion against unthreading.

7. A prosthesis according to claim 1 wherein the proximal tibial component further includes a stem portion extending inferiorly from the head portion and adapted to be received in the medullary cavity of the tibial shaft.

8. A prosthesis according to claim 1 and further comprising a tibial shaft component adapted to replace a resected portion of the proximal tibial shaft and having a stem portion at its distal end adapted to be received in the medullary cavity of the vestigial tibial shaft, and means for connecting the proximal end of the tibial shaft component to the inferior end of the proximal tibial component.

9. A prosthesis according to claim 8 wherein the coupling means includes a tapered joint and a retaining collar engaging a shoulder on the shaft component, threaded onto the proximal tibial component and locked to the proximal tibial component against unthreading.

10. A prosthesis according to claim 1 and further comprising a proximal femoral component adapted to replace a resected proximal portion of the femur and including a body portion and a neck portion, the neck portion having a male tapered stem adapted to receive a prosthetic hip joint ball component; a proximal femoral shaft component adapted to replace a resected portion of the proximal femoral shaft; and means for connecting the proximal end of the shaft component to the proximal femoral component.

11. A prosthesis according to claim 10 wherein the coupling means includes a tapered joint and a retaining collar engaging a shoulder on the shaft component, threaded onto the proximal femoral component and locked to the proximal femoral component against unthreading.

12. A prosthesis according to claim 1 and further comprising a proximal femoral component adapted to replace the proximal femoral head and including a body portion and a neck portion, the neck portion having a male tapered stem adapted to receive a prosthetic hip joint ball component; a femoral shaft component adapted to replace the femoral shaft; means for connecting the proximal end of the femoral shaft component to the proximal femoral component; and means for connecting the distal end of the femoral shaft component to the distal femoral component.

13. A prosthesis according to claim 12 wherein both of said connecting means comprise a tapered joint and a retaining collar engaging a shoulder on the shaft component, threaded onto the respective distal and proximal femoral components and locked to them against unthreading.

* * * * *